(12) United States Patent
Anastasijevic et al.

(10) Patent No.: US 9,090,984 B2
(45) Date of Patent: Jul. 28, 2015

(54) PROCESS AND APPARATUS FOR PRODUCING HYDROGEN

(71) Applicants: Nikola Anastasijevic, Altenstadt (DE); Jan Holst, Oberursel (DE); Andreas Orth, Friedrichsdorf (DE); Markus Schuster, Stuttgart (DE); Bernd Schurtakow, Friedrichsdorf (DE); Michael Stroeder, Frankfurt am Main (DE)

(72) Inventors: Nikola Anastasijevic, Altenstadt (DE); Jan Holst, Oberursel (DE); Andreas Orth, Friedrichsdorf (DE); Markus Schuster, Stuttgart (DE); Bernd Schurtakow, Friedrichsdorf (DE); Michael Stroeder, Frankfurt am Main (DE)

(73) Assignee: OUTOTEC (FINLAND) OY, Espoo (FI)

( * ) Notice: Subject to any disclaimer, the term of this patent is extended or adjusted under 35 U.S.C. 154(b) by 0 days.

(21) Appl. No.: 14/362,629

(22) PCT Filed: Nov. 28, 2012

(86) PCT No.: PCT/EP2012/073764
§ 371 (c)(1),
(2) Date: Jun. 4, 2014

(87) PCT Pub. No.: WO2013/083445
PCT Pub. Date: Jun. 13, 2013

(65) Prior Publication Data
US 2014/0332402 A1 Nov. 13, 2014

(30) Foreign Application Priority Data
Dec. 5, 2011 (FI) .................................... 20110409

(51) Int. Cl.
*B01D 53/32* (2006.01)
*B03C 3/16* (2006.01)
(Continued)

(52) U.S. Cl.
CPC ............... *C25B 15/08* (2013.01); *B01D 53/323* (2013.01); *B01D 53/8671* (2013.01); *B03C 3/017* (2013.01); *B03C 3/16* (2013.01); *C01B 13/0207* (2013.01); *C07C 1/12* (2013.01); *C25B 1/04* (2013.01); *C25B 9/06* (2013.01); *B01D 2256/16* (2013.01); *B01D 2257/104* (2013.01); *Y02C 20/20* (2013.01); *Y02E 60/366* (2013.01)

(58) Field of Classification Search
CPC ................................. B01D 53/323; B03C 3/16
See application file for complete search history.

(56) References Cited

U.S. PATENT DOCUMENTS 3,838,553 A 10/1974 Doherty
5,484,512 A 1/1996 Sasaki et al.
(Continued)

FOREIGN PATENT DOCUMENTS

DE 4201033 A1 7/1993
WO WO 2011056142 A1 5/2011

OTHER PUBLICATIONS

Smolinka, "Wasserstoff aus Elektrolyse—ein technologischer Vergleich der alkalischen and PEM-Wasserelektrolyse", FVS Workshop 2007, Dec. 2007, pp. 67-81.
(Continued)

*Primary Examiner* — Nicholas A Smith
(74) *Attorney, Agent, or Firm* — Leydig, Voit & Mayer, Ltd.

(57) ABSTRACT

A process for producing hydrogen for use in a subsequent methanation process includes electrochemically converting water into hydrogen and oxygen. The hydrogen is depleted with electrolyte aerosols. Then, the electrolyte aerosols are separated from the depleted hydrogen in a wet electrostatic precipitator in a hydrogen atmosphere.

17 Claims, 3 Drawing Sheets

(51) Int. Cl.

| | |
|---|---|
| *C25B 15/08* | (2006.01) |
| *C07C 1/12* | (2006.01) |
| *C25B 1/04* | (2006.01) |
| *B03C 3/017* | (2006.01) |
| *B01D 53/86* | (2006.01) |
| *C01B 13/02* | (2006.01) |
| *C25B 9/06* | (2006.01) |

(56) References Cited

U.S. PATENT DOCUMENTS

| | | |
|---|---|---|
| 6,110,256 A | 8/2000 | Reynolds et al. |
| 6,221,136 B1 * | 4/2001 | Liu et al. .................. 96/66 |
| 6,579,349 B1 | 6/2003 | Ting et al. |
| 2009/0114092 A1 | 5/2009 | Bengtsson et al. |
| 2011/0253550 A1 | 10/2011 | Hoffmann |

OTHER PUBLICATIONS

Chang, et al., Removal of sulfuric acid aerosol in a wet electrostatic precipitator with single terylene or polypropylene collection electrodes, Journal of Aerosol Science, vol. 42, May 18, 2011, pp. 544-554.

\* cited by examiner

PROCESS AND APPARATUS FOR PRODUCING HYDROGEN

CROSS-REFERENCE TO PRIOR APPLICATIONS

This application is a U.S. National Phase Application under 35 U.S.C. §371 of International Application No. PCT/EP2012/073764 filed on Nov. 28, 2012, and claims benefit to Finnish Patent Application No. 20110409 filed on Dec. 5, 2011. The International Application was published in English on Jun. 13, 2013 as WO 2013/083445 A1 under PCT Article 21(2).

FIELD

The present invention is directed to the production of hydrogen, in particular for the use in a subsequent methanation process, wherein water is electrochemically converted into hydrogen and oxygen, wherein the hydrogen is depleted with electrolyte aerosols and wherein the electrolyte aerosols are subsequently separated from the hydrogen.

BACKGROUND

The electrochemical production of hydrogen is performed by alkaline electrolysis. A byproduct is oxygen. When the hydrogen exits the electrolyser, aerosols (small droplets) of the electrolyte, which is usually a solution of potassium hydroxide, are carried over with the gas stream. The concentration of the potassium hydroxide in the hydrogen usually is between 3.0 mg/m$^3$ and 5.0 mg/m$^3$ depending on the structure of the electrolyser and applied electrolysis conditions. A description of the electrolytical production of hydrogen is given in Smolinka, T: "Wasserstoff aus Elektrolyse—ein technologischer Vergleich der alkalischen and PEM-Wasserelektrolyse", FVS Workshop, 2007.

It is very important to remove the potassium hydroxide from the product gas in order to avoid problems in the subsequent process steps. Potassium hydroxide concentrations (>1.0 mg/m$^3$) may cause corrosion on metal elements. This is in particular relevant for subsequent compressors necessary to provide the pressure required for a downstream process as e.g. the methanation process or the direct feed of hydrogen gas into methane gas distribution system. In addition, catalysts may be deactivated and the sealing properties of pipe parts such as valves, etc. may be impaired by crystallization of the potassium hydroxide. Therefore, hydrogen gas that contains droplets of potassium hydroxide aerosols is not suitable for further use.

It is, therefore, known to remove the potassium hydroxide from the product gas by means of a gas scrubber usually located between the electrolyser and the compressor prior to a further use. The removal of the potassium hydroxide is positively influenced by introducing demineralized water which is enriched with the potassium hydroxide and thus can be recycled to the electrolysis process as feed water.

In order to provide for a safe operation, there must be an excess pressure on the suction side of the compressor as compared to the ambient pressure of at least 0.5 kPa gauge. It must be prevented that during the use of the compressor a vacuum is created on the suction side which in the case of leakage in the system will allow air (oxygen) to enter. This may create an explosive gas mixture.

The usually applied gas scrubbers in combination with a low-pressure electrolyser, however, have the following problems: Either, the internal pressure loss of the apparatus is too high so that—depending on the pressure in the electrolysis step—the required excess pressure cannot be maintained. In other types of the gas scrubber the separation efficiency with regard to potassium hydroxide is not high enough to provide the required purity of less than 1.0 mg/m$^3$. Relevant for the separation efficiency with regard to potassium hydroxide aerosols is the size of the droplets. Common gas scrubbers can remove potassium hydroxide droplets above a size of about 20.0 µm (diameter) with a low pressure loss. The major part of the droplets having a diameter of less than 20.0 µm that is typical for aerosols, can only be removed by means of a device causing a high pressure drop, such as a venturi scrubber or a fixed bed packing. Such packings, however, involve high pressure losses and are quite expensive.

A further contaminant of the hydrogen gas stream is oxygen, which is the second gas product of water electrolysis. This contamination is created by incompletely gastight diaphragms between the anode and the cathode of the electrolyser. The oxygen content in the hydrogen gas is, dependent on the operation state, between 0.0 and 2.0 vol.-%, corresponding to about 50.0% of the lower explosion limit. Values above 2.0 vol.-% are not admissible in the system and will consequently lead to an automated safety shutdown of the electrolysers. Elevated oxygen concentrations in the hydrogen gas reduce gas purity and may also be detrimental to catalysts if the hydrogen is used in subsequent processes. Usually, the oxygen is removed after the scrubbing step by catalytic oxidation converting it with hydrogen to water vapor.

The final step of the hydrogen gas treatment either for the use in a downstream process or for direct feed of hydrogen gas into methane gas distribution system is the gas drying. Usually, adsorption dryers filled with a drying agent like silicagel are used to remove the remaining moisture from the hydrogen. Usually two drying units are provided in parallel and operated one at a time to ensure a continuous operation. One unit is used while the other unit is regenerated to remove the adsorbed water vapor.

SUMMARY

In an embodiment, the present invention provides process for producing hydrogen for use in a subsequent methanation process. Water is electrochemically converted into hydrogen and oxygen. The hydrogen is depleted with electrolyte aerosols. Then, the electrolyte aerosols are separated from the depleted hydrogen in a wet electrostatic precipitator in a hydrogen atmosphere.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
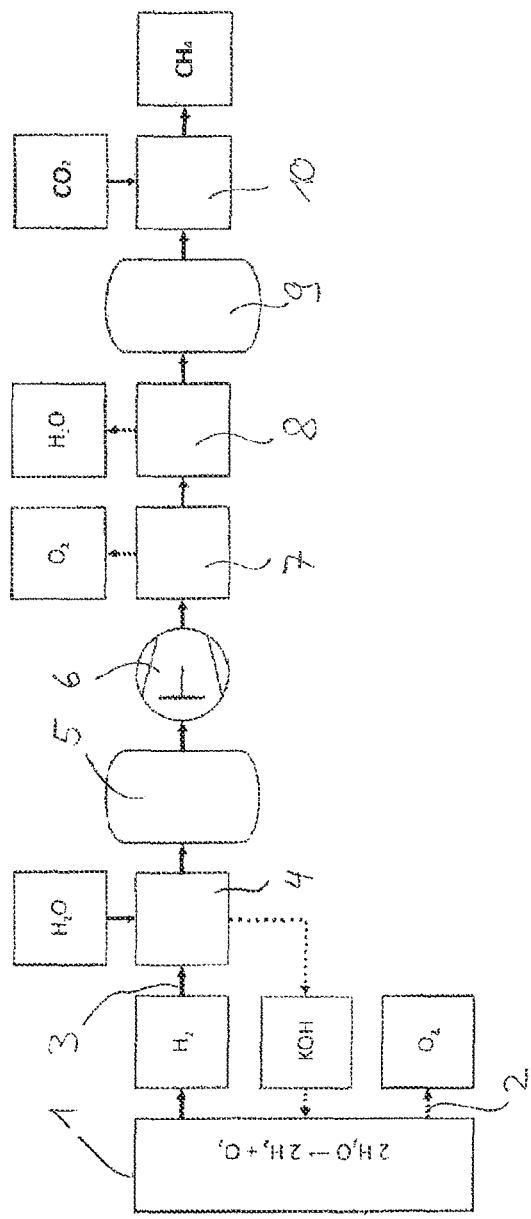
FIG. 1 is a schematic flow sheet of the process according to an embodiment of the present invention.

In an embodiment, the present invention facilitates the removal of contaminants from the hydrogen product gas of the electrolysis without creating a major pressure drop and simplies the further cleaning process described above.

In an embodiment, the separation of the electrolyte droplets and/or aerosols from the depleted hydrogen is performed in a wet electrostatic precipitator (W-ESP) in a hydrogen atmosphere. Accordingly, the standard gas scrubber is replaced by a wet electrostatic precipitator. Such a precipitator has high separation efficiency while having very low pressure loss only. Electrostatic precipitators are used in several applications but not yet in relation to hydrogen because there always has been the fear of explosions if hydrogen is exposed to high voltages.

The electrolyte used for producing the hydrogen gas from water preferably is an alkaline electrolyte, in particular potassium hydroxide. In general and in the context of the present invention, however, it is also possible to use other electrolytes including acidic electrolyte, such as $H_2SO_3$ used in the $SO_2$ depolarised hydrogen production.

According to a preferred embodiment of the invention the depleted hydrogen is passed through the precipitator from bottom to top. As water is sprayed into the precipitator to remove the potassium hydroxide collected at a collecting electrode the depleted hydrogen is passed through the precipitator counter currently to the water.

According to an embodiment of the invention the depleted hydrogen is introduced into the lower third of the precipitator, preferably though a gas distributor in order to ensure a uniform distribution over the cross section of the precipitator.

Within the precipitator a discharge electrode is provided which preferably is insulated from the precipitator housing by means of an inert gas buffer. Traditionally, the electrodes are insulated by ceramic insulation, which may break upon the introduction of high voltage. The inert gas buffer is also suitable for high pressures and is not influenced by the voltage level. Preferably, nitrogen is used as inert gas.

In a preferred embodiment of the invention the pressure of the inert gas buffer is maintained at a level between the inside pressure of the precipitator and the ambient pressure surrounding the precipitator. If the pressure is monitored by a respective pressure gauge, a leakage towards the interior of the precipitator, which is operated at a higher pressure than the surrounding atmosphere, can be detected if the pressure in the inert gas buffer rises above a certain level. On the other hand, a leakage to the surrounding atmosphere can be detected if the pressure in the inert gas buffer drops below a certain limit.

Preferably, the area around the insulation of the discharge electrode is heated to avoid the formation of a fluid film over the insulator that could cause a direct current flow between both electrodes (anode and cathode).

While electrolyte aerosols can be reliably removed by the electrostatic precipitator, the oxygen contamination remains. In a preferred embodiment of the invention, the oxygen is removed from the hydrogen gas stream in a first catalytic step in the presence of a palladium (Pd) catalyst. In a subsequent second catalytic step methane is produced from the educts hydrogen and carbon dioxide ($CO_2$, from an external source) in the presence of a catalyst, preferably a nickel (Ni) catalyst.

Preferably, the first catalytic stage is operated at a temperature of 300 to 350° C. and/or the second catalytic stage is operated at a temperature of 450 to 550° C., in particular about 500° C.

The methanation process is highly exothermic. If the temperature in the reactor rises to a very high temperature, the catalyst may be destroyed. Therefore, the invention proposes to introduce steam together with the educts $CO_2$ and hydrogen into the first catalytic stage. This additional steam shifts the equilibrium of the reaction towards the side of the educts which reduces the conversion of hydrogen and carbon dioxide.

Alternatively, it is possible to recycle a partial stream of the methane and water produced in the second catalytic stage to the inlet of the first catalytic stage. Thereby, the concentration of the educts (hydrogen and carbon dioxide) is reduced, thereby reducing the conversion rate.

An embodiment of the invention also is directed to an electrostatic precipitator which may be used in a process as described above. Such electrostatic precipitator comprises a housing, a discharge electrode (cathode), a collecting electrode (anode), an inlet for water, an inlet for depleted hydrogen, an outlet for water and an outlet for purified hydrogen.

Preferably, the discharge electrode is insulated from the ceiling of the housing by an inert gas buffer, wherein according to the invention a pressure detector is provided for measuring the pressure of the inert gas buffer and/or a hydrogen analysis system is provided for measuring the hydrogen concentration inside the inert gas buffer.

In a preferred embodiment of the invention the precipitator is vertically oriented wherein the hydrogen is introduced into a lower third of the housing, preferably via a distributor plate, and wherein the water is introduced from above in order to create a counter current flow.

In order to increase the efficiency of the apparatus, the electrostatic precipitator preferably has several precipitation modules each comprising a system of a discharge electrode and a collecting electrode.

In the process of producing hydrogen for the use in a downstream process as e.g. the methanation process as shown in the flow sheet of FIG. 1 water ($H_2O$) and an alkaline electrolyte, in particular potassium hydroxide (KOH), are introduced into an electrolyser 1 in which the water is split by electrolysis into hydrogen ($H_2$) and oxygen ($O_2$). The oxygen is withdrawn via line 2. The hydrogen gas stream is withdrawn via line 3 wherein droplets and aerosols of the electrolyte are carried over with the hydrogen gas stream. The thus depleted hydrogen is introduced into a wet electrostatic precipitator (ESP) 4 which will be described in more detail below. In the precipitator 4 the electrolyte (KOH) is removed from the hydrogen and recycled to the electrolyser 1.

The purified hydrogen gas stream then is introduced into an (optional) buffer tank 5 and pressurized in a compressor 6. The pressurized hydrogen stream which still contains a minor oxygen contamination is introduced into a catalytic reactor 7 wherein the oxygen is removed by reaction with hydrogen and generation of water vapor. Subsequently the hydrogen is dried in reactor 8 and stored in hydrogen pressure storage tank 9 before the introduction into a downstream process 10. If the downstream process 10 represents a methanation reactor, the hydrogen is reacted with carbon dioxide ($CO_2$) to produce methane and water.

Figure 2:
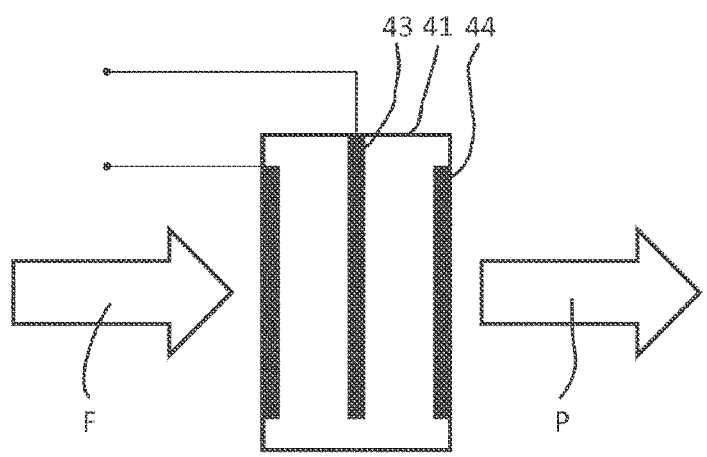
FIG. 2 is a schematic section through a precipitator according to an embodiment of the present invention.

The general configuration and the working principle of the wet electrostatic precipitator applied within this invention are shown in FIG. 2.

The wet electrostatic precipitator consists of a housing 41, a discharging electrode 43 and a collecting electrode 44 on that the aerosol is deposited. The feed F contains depleted hydrogen gas, contaminated with aerosol droplets and a wash liquid (water) that purges the collecting electrode. As products P of the scrubbing process in a wet electrostatic precipitator, there are purified hydrogen gas and wash liquid, enriched by the removed contaminants. The addition of the depleted gas can be on top of the wet electrostatic precipitator, as well as on the bottom. Dependent on specific requirements, co-current flow between gas and wash liquid is possible, as well as counter or cross flow.

Figure 3:
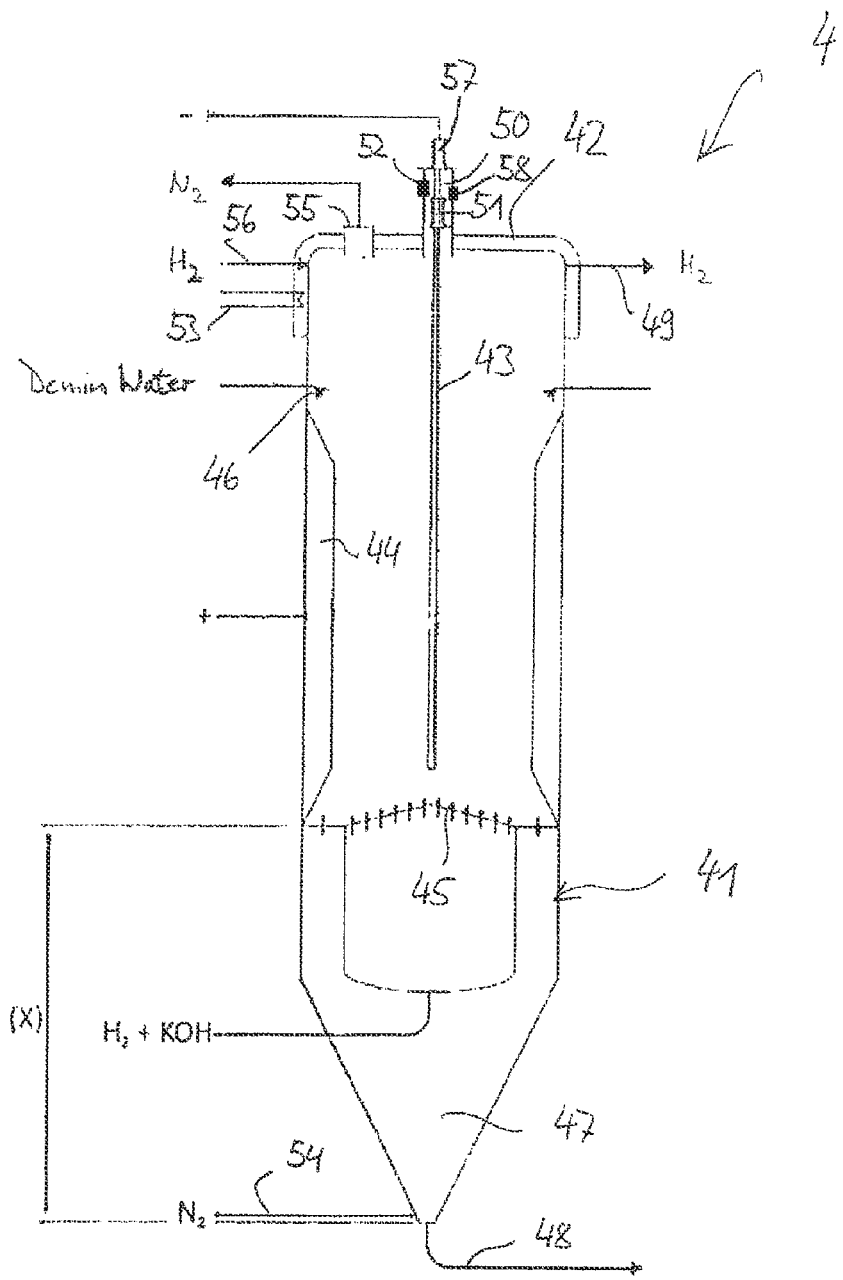
FIG. 3 is a schematic section through a wet electrostatic precipitator according to an embodiment of the present invention.

As shown in FIG. 3 the vertically oriented wet precipitator 4 comprises a housing 41 with a ceiling 42 through which a negatively poled discharge electrode 43 (cathode) is introduced and a positively poled collecting electrode 44 (anode) provided around the discharge electrode on the inner wall of the housing 41.

According to a preferred embodiment of the invention, the hydrogen, produced at the cathode of the electrolysis cell, is passed through the precipitator 4 from bottom to top. Therefore the depleted hydrogen is introduced through line 3 (hydrogen inlet) into the lower third of the precipitator 4 (region X in relation the apparatus height). A uniform distribution of the feed gas over the cross section of the precipitator 4 is realized by a gas distributor 45.

As applied wash liquid, demineralized water is introduced through spraying nozzles 46 (water inlet) above the collecting electrode 44 to remove the deposited potassium hydroxide collected there. Thereby, a counter current flow between the water and the hydrogen rising in the precipitator is created. A collecting sump 47 intercepts the water including the potassium hydroxide which is withdrawn through line (water outlet) 48 and then can be used as feed water for the electrolyser 1. Purified hydrogen is withdrawn through line (hydrogen outlet) 49 at the top of the precipitator 4.

Within the precipitator a high-voltage discharge electrode 43 is provided. The feed-through of the discharge electrode into the precipitator housing 41 is traditionally realized by a ceramic based first high-voltage isolator 51. This assembly inhibits an electrical contact between discharging electrode, precipitator housing and collecting electrode. Preferably, the ceiling 42 around the first high-voltage isolator 51 of the discharge electrode is heated by means of a heater 53 to avoid the formation of a condensate film over the isolator that could provide a conductive connection between both electrodes (anode and cathode) across the insulator.

The application of wet electrostatic precipitators with a hydrogen atmosphere inside demands stronger requirements concerning the separation of hydrogen atmosphere inside the precipitator and the environment to avoid the formation of explosive mixtures (oxyhydrogen gas) and the contamination of product gas if ambient air diffuses into hydrogen in case of leakages at the high-voltage isolator 51 of the discharge electrode. Therefore, a special design is applied for the feed-through of the discharge electrode within the present invention.

An atmosphere separator chamber 50 is provided around the high-voltage isolator 51 of the discharge electrode 43 (inner isolator), filled with an inert gas such as nitrogen, carbon dioxide or argon. Therefore, a second high-voltage isolator 57 for the discharge electrode (outer isolator) on top of the inert gas buffer is needed. The inert gas buffer 50 avoids a direct hydrogen exposition to the environment and the formation of an explosive mixture due to inner insulator leakage.

In a preferred embodiment of the invention the pressure of the inert gas buffer 50 is maintained at a pressure level between the internal pressure of the precipitator and the ambient pressure surrounding the precipitator. If, for example, the excess pressure inside the precipitator 4 is 2.0 kPa (g), the excess pressure inside the inert gas buffer 50 should be 1.0 kPa (g)±0.5 kPa. This buffer is also suitable for higher pressures and is not influenced by the voltage level.

The pressure into the inert gas chamber is monitored and controlled by a respective pressure gauge 52. Pressure fluctuations as a result of temperature variations are balanced by local temperature measurement combined with the calculation of a pressure-temperature-correlation. A complete automatic control demands pressure measurements inside the precipitator, in the inert gas buffer and in the atmosphere surrounding the precipitator.

Leakages through both high-voltage isolators 51 and 57 can be detected by pressure changes inside the inert gas buffer 50. In case of a leakage at the inner isolator 51 that separates the interior of the precipitator and the inert gas chamber, the pressure of the inert gas chamber raises until the higher pressure level of precipitator interior is reached. On the other hand, a leakage at the outer isolator 57 that separates the inert gas chamber and the environment can be detected if the pressure in the inert gas buffer 50 drops until it reaches ambient pressure. A hydrogen gas analyzer 58 for measurements inside the inert gas buffer 50 completes the monitoring system.

In case of plant shutdowns, the precipitator 4 is cleaned (inertisized) by purging preferably with nitrogen. In this case, nitrogen is tangentially introduced into the bottom of the precipitator 4 via line 54 wherein turbulences should be avoided. Because of its higher density the nitrogen pushes the lighter hydrogen to the upper portion of the precipitator 4 from where it is withdrawn through outlet 55. The different densities of nitrogen and hydrogen create a piston like flow. If the nitrogen is introduced with a lower temperature the difference in density is even further increased. The same effect is used if the precipitator should be restarted. In this case the hydrogen is tangentially introduced into the upper part of the precipitator 4 via line 56 in order to press the nitrogen downwards out of the precipitator through line 54.

The wet electrostatic precipitator 4 is constructed as a vertically oriented tube and can be operated with atmospheric electrolysis at a slightly elevated pressure of about 2.0 kPa (g) or at a higher pressure of 0.1 MPa to 10.0 MPa and beyond. Corresponding to the volume flow of the gas stream that needs to be purified the precipitator may comprise one or more precipitation modules each consisting of a respective discharge electrode 43 and collecting electrode 44. The electrostatic precipitator is operated at a voltage of 5.0 kV to 130.0 kV, preferably at a voltage of 60.0 kV to 120.0 kV.

By means of the wet electrostatic precipitator 4 the concentration of the electrolyte, e.g. potassium hydroxide, in hydrogen can be reduced below 1.0 mg/Nm$^3$, preferably to less than 0.5 mg/Nm$^3$. The wet electrostatic precipitator can also be used to remove electrolyte aerosols from the oxygen being the second product of the electrolysis.

In order to increase the efficiency and to adapt the apparatus to gas volume flow, the electrostatic precipitator preferably has several precipitation modules each comprising a system of a discharge electrode and a collecting electrode.

A preferred embodiment of the present invention provides for a two-step methanation process. In a first catalytic stage the oxygen is removed in the presence of a palladium (Pd) catalyst at a temperature of 300 to 350° C. In the second stage the actual methanation is performed in the presence of a catalyst, preferably a nickel (Ni) catalyst at a temperature of preferably about 500° C. The energy released upon the catalytic burning of the oxygen can be used as activation energy to start the methanation process.

In order to protect the catalyst, it is necessary to regulate the temperature in the very exothermic methanation process. In a first variant of the present process a partial stream of the product gases (methane and water) is recirculated to the inlet of the methanation reactor in order to reduce the concentration of the educts (hydrogen and carbon dioxide). In a preferred second modification of the process, steam is introduced together with the educt gas stream to regulate the temperature increase. The steam shifts the equilibrium of the reaction to the side of the educts thereby reducing the conversion of hydrogen and carbon dioxide and thus the temperature increase.

Usually the product gas of the electrolysis is dried in a silicagel dryer. In a preferred embodiment of the present invention, this drying step can be suppressed by increasing the capacity of the compressor. If the compressor operates at a higher pressure (for example 20 bar) the volume ratio of the water in the product gas is reduced as part of the water condensates. The volume ratio of the water can be further reduced by additional cooling as the saturated vapor pressure is further reduced. The desired gas purity of 99.91% can be achieved using a pressure of 2.0 MPa and a gas temperature of 15.0° C.

With the present invention, the hydrogen gas to be used in a downstream process, as e.g. the methanation, can be purified using a very simple and reliable system. A pressure loss is avoided which facilities the further handling of the gas streams.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMBERS 1 electrolyser
2 line
3 line (hydrogen inlet)
4 electrostatic precipitator
5 buffer store
6 compressor
7 catalytic reactor
8 dryer
9 $H_2$ pressure storage
10 methanation reactor
41 housing
42 ceiling
43 discharge electrode
44 collecting electrode
45 gas distributor
46 spraying nozzle (water inlet)
47 collecting sump
48 line (water outlet)
49 line (hydrogen outlet)
50 nitrogen buffer
51 inner high-voltage isolator
52 pressure gauge
53 heater
54 line
55 outlet
56 line
57 outer high-voltage isolator
58 hydrogen gas analyzer
F feed components
P product components
X lower third of precipitator 4

The invention claimed is:

1. A process for producing hydrogen for use in a subsequent methanation process, the process comprising:
   electrochemically converting water into hydrogen and oxygen, wherein the hydrogen is depleted with electrolyte aerosols, and then
   separating the electrolyte aerosols from the depleted hydrogen in a wet electrostatic precipitator in a hydrogen atmosphere.

2. The process according to claim 1, wherein the electrolyte is an alkaline electrolyte.

3. The process according to claim 1, wherein the depleted hydrogen is passed through the precipitator from bottom to top.

4. The process according to claim 1, wherein the depleted hydrogen is passed through the precipitator counter currently to water sprayed into the precipitator.

5. The process according to claim 1, wherein the depleted hydrogen is introduced into a lower third of the precipitator.

6. The process according to claim 1, wherein a discharge electrode is provided within the precipitator and wherein the discharge electrode is insulated from a housing of the precipitator by means of an inert gas buffer.

7. The process according to claim 6, wherein a pressure of the inert gas buffer is maintained at a level between an inside pressure of the precipitator and an ambient pressure surrounding the precipitator.

8. The process according to claim 6, further comprising heating an area around an insulation of the discharge electrode.

9. The process according to claim 1, further comprising removing oxygen from a hydrogen gas stream in a first catalytic step in a presence of a palladium (Pd) catalyst and producing methane in a subsequent second catalytic step from educts carbon dioxide and hydrogen.

10. The process according to claim 9, wherein steam is introduced together with $CO_2$ and hydrogen into the first catalytic step.

11. An electrostatic precipitator for use in a process according to claim 1, comprising:
    a housing,
    a discharge electrode,
    a collecting electrode,
    an inlet for water,
    an inlet for depleted hydrogen,
    an outlet for water, and
    an outlet for purified hydrogen, wherein the discharge electrode is insulated from a ceiling of the housing by an inert gas buffer.

12. The electrostatic precipitator according to claim 11, further comprising at least one of: a pressure detector configured to measure a pressure of the inert gas buffer and a hydrogen analysis system configured to measure a hydrogen concentration inside the inert gas buffer.

13. The electrostatic precipitator according to claim 11, wherein the precipitator is vertically oriented.

14. The electrostatic precipitator according to claim 11, further comprising a gas distributor disposed in a lower third of the housing for introducing the depleted hydrogen.

15. The electrostatic precipitator according to claim 11, having several precipitation modules each comprising a system of a discharge electrode and a collecting electrode.

16. The process according to claim 2, wherein the alkaline electrolyte is potassium hydroxide.

17. The process according to claim 5, wherein the depleted hydrogen is introduced into the precipitator through a gas distributor.

* * * * *